United States Patent
Luloh

[11] Patent Number: 5,425,730
[45] Date of Patent: Jun. 20, 1995

[54] ILLUMINATION CANNULA SYSTEM FOR VITREOUS SURGERY

[76] Inventor: K. P. Luloh, 176 Citation Ct., Lake Mary, Fla. 32746

[21] Appl. No.: 197,479
[22] Filed: Feb. 16, 1994
[51] Int. Cl.⁶ ............................................. A61B 17/36
[52] U.S. Cl. ........................................ 606/15; 606/4; 606/16; 604/21
[58] Field of Search .......................... 606/4–6, 606/15, 16; 604/20, 21

[56] References Cited

U.S. PATENT DOCUMENTS

| | | |
|---|---|---|
| 3,728,998 | 4/1973 | Heine . |
| 3,821,510 | 6/1974 | Muncheryan . |
| 3,982,541 | 9/1976 | Liesperawce, Jr. ............. 606/4 X |
| 4,207,874 | 6/1980 | Choy ............................. 604/21 X |
| 4,222,375 | 9/1980 | Martinez . |
| 4,269,192 | 5/1981 | Matsuo . |
| 4,311,138 | 1/1982 | Sugarman . |
| 4,331,130 | 5/1982 | Lewicky . |
| 4,551,129 | 11/1985 | Coleman et al. . |
| 4,567,882 | 2/1986 | Heller . |
| 4,641,912 | 2/1987 | Goldenberg . |
| 4,686,979 | 8/1987 | Gruen et al. . |
| 4,820,264 | 4/1989 | Matsui et al. ............... 604/21 |
| 5,123,902 | 6/1992 | Müller ....................... 604/20 X |
| 5,129,895 | 7/1992 | Vassiliades ................ 606/6 |
| 5,334,190 | 8/1994 | Seiler ......................... 606/5 |

FOREIGN PATENT DOCUMENTS

WO11054 10/1990 WIPO ............................. 606/6

OTHER PUBLICATIONS

Koch et al. "The Retinal Irradiance and Special Properties of the Multiport Illumination System for Vitreous Surgery" 116 AM. J. Ophthalmology 489–496 (Oct. 1993).

Primary Examiner—Peter A. Aschenbrenner
Attorney, Agent, or Firm—Warren L. Franz; James H. Beusse

[57] ABSTRACT

An illumination cannula system for vitreous surgery. The cannula system has a plurality of illuminated cannula ports, each including a multiplicity of optical fibers annularly arranged about a central conduit channel provided with a double seal onto which a sleeve connector or boot of an infusion line adapter or sealing plug can be attached. The adapter includes an extended tube for discharging fluid beyond the terminations of the fibers. The double seal provides a convenient, positive snap-action sealing connection. Identical configurations of the cannula ports enable post-placement selection and interchange of infusion and instrumentation ports.

20 Claims, 3 Drawing Sheets

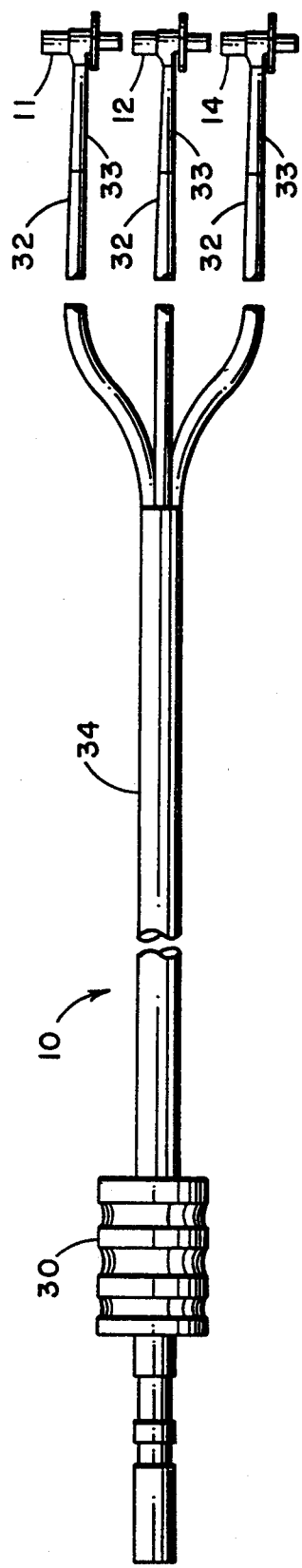
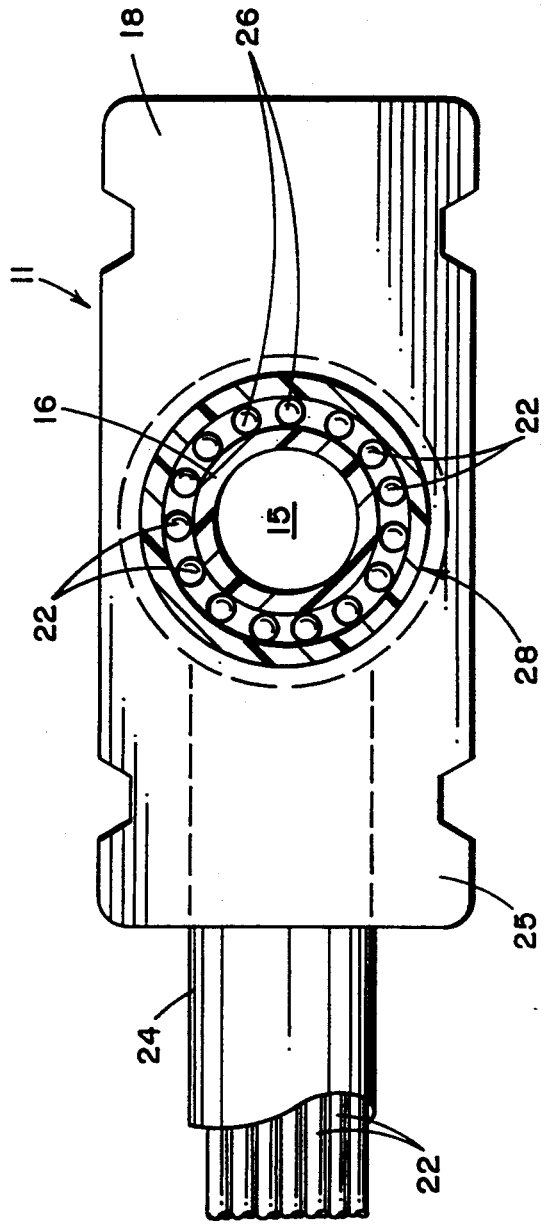

ILLUMINATION CANNULA SYSTEM FOR VITREOUS SURGERY

The present invention relates generally to an illumination cannula system for closed vitreous surgery; and, in particular, to a cannula system providing multiple illuminated sclerotomy ports, interchangeably usable for liquid or gas fluid infusion or insertion of surgical instruments during surgery.

BACKGROUND OF THE INVENTION

Pars plana vitrectomy is a closed vitreous surgical technique for operating on the eye wherein the surgical field is observed through the pupil and instrumentation is inserted into the vitreous cavity through surgical cuts or sclerotomies which are fitted with ports to prevent leakage of intraocular fluid. Visualization is accomplished using a viewing system, such as a binocular indirect opthalmomicroscope system described in U.S. Pat. No. 4,710,000 or 5,009,487. Intraocular pressure is regulated by infusion of fluid through a separate sclerotomy port. Illumination of the back of the eye or fundus may be originated from an external source through the pupil, or internally through fiber optics. It has been generally recognized that internal illumination with fiber optics is superior to external illumination and is not as dependent on variances in pupillary dilatation or clarity of the ocular media. A frequent practice is to employ a three- or four-port procedure, utilizing one or two ports for exchangeable working instruments, another port for infusion, and another port for illumination using a source such as a ceiling light available from D.O.R.C. Company, Geervleit, The Netherlands, or a chandelier system available from Grieshaber, Schafthausen, Switzerland.

It is known to incorporate optical fibers into the working end of the surgical instrument. This eliminates the need for a separate illumination port and offers the advantage of directing the light beam together with the instrument onto the target site. Instrument sizes must, however, be correspondingly increased and larger sclerotomies may be necessary. An alternative procedure is to employ an illuminated infusion cannula to integrate the infusion and illumination functions at a single point.

One example of a combined infusion cannula and illumination source is given in U.S. Pat. No. 4,820,264. The '264 device comprises an infusion channel through which light transmitting fibers are passed for directing light into the eyeball at the point of discharge of the intraocular irrigating solution. Such illumination is not automatically directed by manipulation of the cutting instruments. Moreover, the fibers are run directly within the infusion channel, and illumination and infusion portions are non-separable near the eye.

The integrated lighting concept has been extended to provide illuminated cannulas at multiple ports having channels through which either infusion fluids or surgical instruments can be passed. Such a multiport illuminated cannula system is described in Koch, et al. "The Retinal Irradiance and Spectral Properties of the Multiport Illumination System for Vitreous Surgery" appearing at 116 Am. J. Ophthalmology 489–496 (October 1993) and is the subject of Koch's copending application U.S. Ser. No. 07/750,114, entitled "Illuminated Leading Probe Device and Method," the disclosures of both of which are incorporated herein by reference. Such multiport illuminated cannula comprises a plurality of light transmitting fibers annularly arranged about a central instrument-receiving working channel. Such device has the advantage that fibers are located external to the working channel. The channels are, however, awkward to seal upon instrument removal and, if used for infusion purposes, lack expedient infusion tube interfaces and, as in the '264 device, discharge fluid directly at the optical fiber terminations, thereby interfering with illumination.

SUMMARY OF THE INVENTION

It is an object of the invention to provide an improved illumination cannula system and method of illumination of the operating site for closed vitreous surgery, and the like.

In accordance with one aspect of the invention, an illumination cannula system for vitreous surgery comprises a plurality of illuminated cannula ports, each including a multiplicity of optical fibers annularly arranged about a central conduit channel provided with a double seal onto which a sleeve connector or boot of an infusion line adapter or sealing plug can be attached. Alternatively, the conduit can be left open for receiving the working end of a surgical instrument. The adapter includes an extended tube for discharging fluid beyond the terminations of the fibers. The double seal provides a convenient, positive snap-action sealing connection. Identical configurations of the cannula ports enable post-placement selection and interchange of infusion and instrumentation ports.

In another aspect of the invention, the central conduit channel of each cannula port may incorporate a self-closing valve member to further prevent escape of fluid from the fundus when the infusion line adapter or surgical instrument is withdrawn. A preferred embodiment, described below, utilizes a diaphragm valve with an iris flap opening and provides a tapered enlargement at the mouth of the channel to accommodate flap deflections and guide tool insertion.

BRIEF DESCRIPTION OF THE DRAWINGS

Embodiments of the invention have been chosen for purposes of illustration and description, and are shown in the accompanying drawings, wherein:

FIG. 1 is an overall view of an illumination cannula in accordance with the apparatus of the invention, suitable for use in practicing the method of the invention;

FIG. 2 is an enlarged bottom plan view of one of the probes of the apparatus of FIG. 1;

Throughout the drawings, like elements are referred to by like numerals.

DETAILED DESCRIPTION OF PREFERRED EMBODIMENTS

Figure 3:
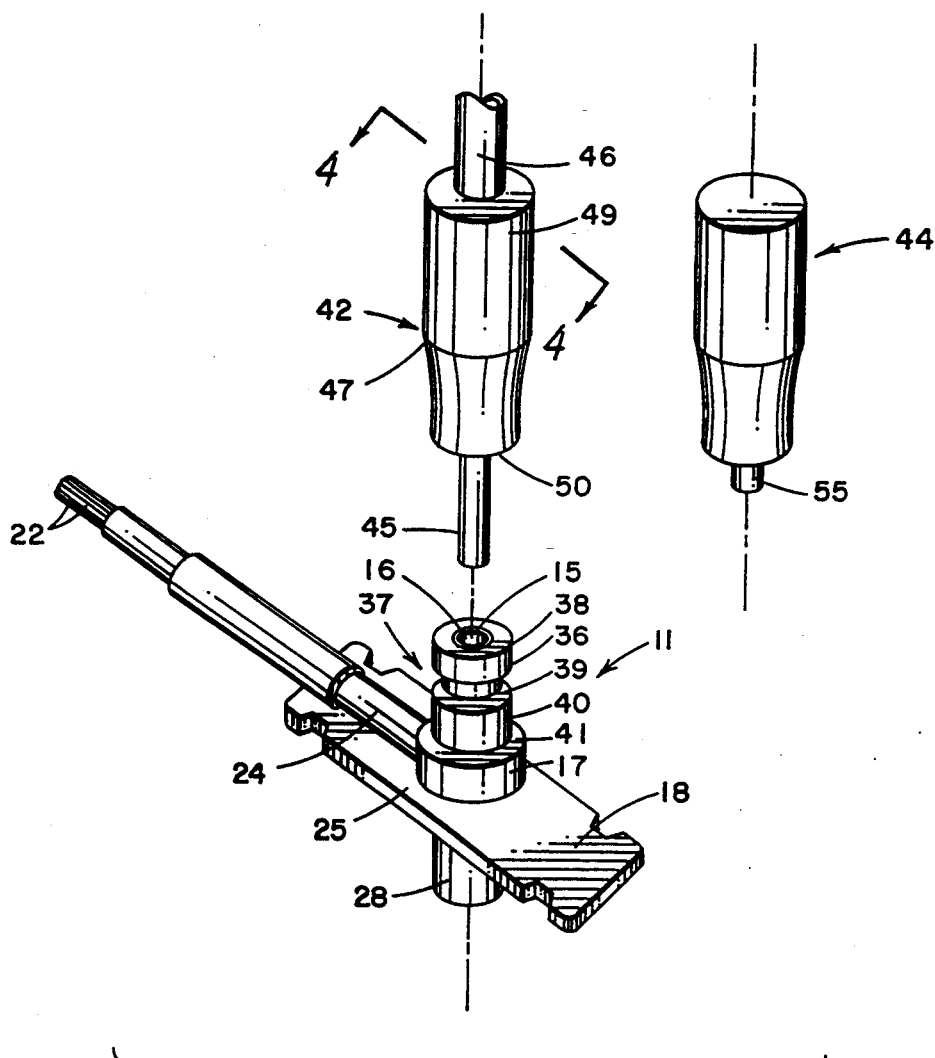
FIG. 3 is an exploded view showing alternative connection of an infusion device or cap to the seal of the apparatus of FIG. 1.
Figure 4:
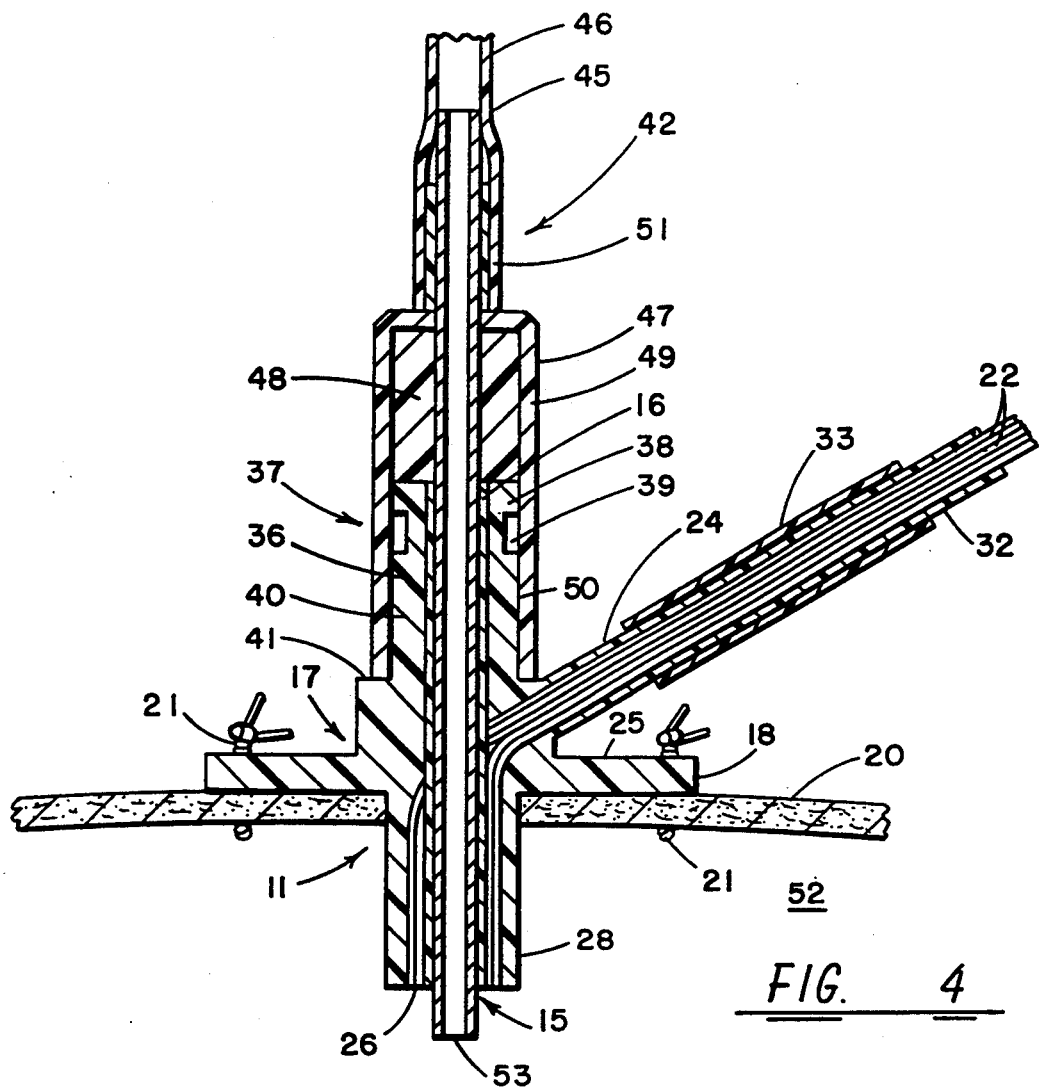
FIG. 4 is a section view taken along the line 4—4 of FIG. 3, of the joined cannula and infusion line adapter apparatus.

A novel multiport illumination cannula system 10 suitable for use in pars plana vitrectomy comprises three lighted cannulas 11, 12, 14 (FIG. 1), which can be anchored in the pars plana, and which include central working channels 15 (FIGS. 3 and 4) constructed for interchangeably receiving infusion or active surgical instruments therein. Each channel 15 is defined by the hollow interior of a length of rigid plastic tubing 16 encased within a plastic shroud 17 that includes an opposite laterally extending notched suture pad or foot plate 18 by which the cannula 11, 12, 14 can be attached to the eyeball wall 20 (FIG. 4). Attachment may be by surgical suture thread 21 or by other known attachment mechanism.

The cannulas 11, 12, 14 are identical. For each cannula 11, 12, 14, a plurality of optical fibers 22 enter shroud 17 at an upwardly and outwardly angled sleeve portion 24 above one wing 25 of pad 18, and terminate at proximal ends 26 annularly, equiangularly-spaced about the outside diameter of tube 16 within a leading probe end 28 of cannula 11. Distal ends of fibers 22 are commonly joined at a known metal connector 30 (FIG. 1) for connection to receive illumination from a single xenon or halogen lamp light source. Connection may be to the light source of a Storz Premiere Vitrectomy unit, or other appropriate known conventional device. The fibers 22 of each cannula 11, 12, 14 are run through a respective fiber optic cable 32 which is coupled to the corresponding sleeve portion 24 by means of a length of shrink tubing 33. The fibers 22 are then merged to run through the hollow of a common length of flexible tubing 34, preferably colored or coated for maximum internal reflectance to minimize light attenuation between light input aperture ends at connector 30 and light output aperture ends at cannula probes 11, 12, 14. There may suitably be 15 or 20 optical fibers 22 arranged about the tube 16 at leading end 28 of each cannula shroud 17. The fibers are preferably lightweight plastic elements of large light-conducting capability and high numeric aperture (greater than 0.6), chosen to provide good wide-angle light coverage while avoiding light toxicity.

The top end 36 of each cannula 11, 12, 14 includes a cylindrical double-seal assembly 37 coaxially annularly disposed about the upper end of tube 16. Assembly 11 is stepped in the axial direction and includes a circular ring-shaped flange upper portion 38 of given outside diameter, a lesser outside diameter cylindrical intermediate portion 39, and a cylindrical lower portion of the same outside diameter as portion 38. A circular ring-shaped shoulder 41 surrounds the base of lower portion 40. Assembly 37 is configured for receiving either an infusion line adapter 42 or a plug 44 in sealing mating relationship thereon.

Adapter 42 comprises a length of metal tubing 45 having an upper end inserted within a proximal end of an infusion line 46 and a lower end insertable through the channel of tube 16. A boot 47, comprising a slug 48 enveloped by a downwardly opening cylindrical shell 49, surrounds an intermediate portion of tube 45. Shell 49 extends below slug 48 to present a downwardly opening cylindrical hollow 50 of inside diameter slightly less than the outside diameter of flange 38 and lower portion 40 of assembly 37. Hollow 50 is dimensioned in an axial direction to be the same as the axial extent of assembly 37 from shoulder 41 to the top of flange 38. Boot 47 is, thus, dimensioned, configured and adapted to snap over double seal assembly 37, with the base of slug 48 brought adjacent to the top of flange 38 and the lower end of tube 45 protruding a short distance beyond the termination of leading end 28 of cannula 11, 12 or 14.

Except for tubes 16 and 45, the cannulas 11, 12, 14 and adapter 42 are suitably made of surgery compatible elastomeric material. A tubular extension 51 of boot 47 extends about a portion of tube 45 above the top of shell 49 to serve as a surface about which the proximal end of hollow tubing of infusion line 46 can be secured. With adapter 42 inserted within cannula 11, 12 or 14 as shown in FIG. 4, tubing 45 is sealingly engaged within tubing 16, for delivery of infusion fluid into the vitreous cavity 52 at a discharge point 53 located below the terminal light-emitting ends 26 of fibers 22. It is noted that fluid discharge, thus, occurs away from the location of internal light source introduction.

Figure 5:
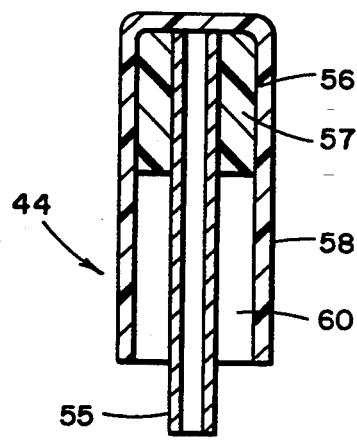
FIG. 5 is a section view, taken along the line 5—5 of FIG. 3, of the plug of FIG. 3.

Plug 44 (FIGS. 3 and 5) includes a length of metal tubing 55 of same diameter as metal tubing 45; however, of shorter axial length. The top of tubing 55 is closed by a cylindrical shell 56 which has a configuration similar to that of shell 49. A slug 57 has the same configuration as slug 48, and together with shell 56 constitutes a similar boot 58 having a downwardly open cylindrical hollow 60 identical with that of hollow 50 of boot 47. Plug 44 may be interchangeably substituted over cannula 11, 12 or 14, in place of adapter 42, with tubing 55 inserted within tubing 16 and shell 56 going over the top end 36 of shroud 17. Unlike the lower end of tube 45 of adapter 42, however, the inserted lower end of tubing 55 does not project below the leading end 28 of cannulas 11, 12, 14.

Cannulas 11, 12 and 14 are identically configured so that maximum flexibility is achieved for the surgical procedure, while minimizing trauma due to introduction and removal of surgical instruments. The system 10 provides for one illumination cannula port at each of three standard pars plana entry sites. This enables the cutting and removal of intraocular tissue in a standard divided system procedure, with one cannula used for infusion, another used for exchangeable introduction and manipulation of working vitreous surgical instruments, and the third used for another instrument or merely as a light-conducting probe. After surgical instruments are introduced through the channel of a cannula, movement of the instrument will cause the light to automatically change direction to the area of interest. Because the cannulas in the pars plana extend only a short distance (about 4 mm) into the vitreal cavity, the distance between the terminal ends of the lighted cannula fibers and the surface of the retina is relatively large, thereby providing a maximally illuminated field. In contrast to the hand-held light pipes, the multiport illumination system 10 allows the surgeon to use both hands to perform active vitreous surgery. Because the three cannulas are identical, the ports used for infusion and introduction of instruments can be exchanged at will, enabling the surgeon to select the best placement for a particular working angle.

Figure 6:
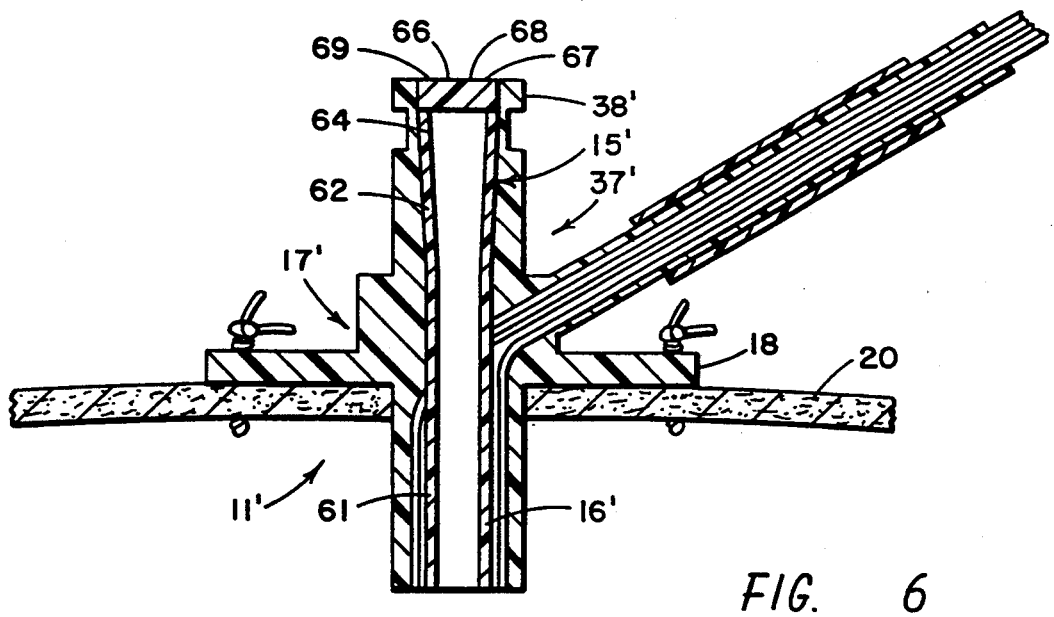
FIG. 6 is a view, as in FIG. 4, of a modified form of the same cannula apparatus.

FIG. 6 shows a modified form 11' of the cannula 11, already described. Cannula 11' has a central working channel 15' which is defined by the hollow interior of a length of rigid plastic tubing 16' encased within a plastic shroud 17' that includes an opposite laterally extending suture pad or foot plate 18, identical with the corresponding suture pad 18 of cannula 11. A lower part of tubing 16' that extends through the sclerotomy is identical with a corresponding lower part of tubing 16, and is a cylindrical tubular section 61 of uniform inside diameter. However, an upper part of tubing 16' includes an enlarged portion having an upwardly and outwardly tapered section 62 extending above the foot plate 18, for about ¼ to ⅓ of the total length of tubing 16'. The inside diameter is correspondingly increased in a continuous taper from a smallest diameter at the transition to the lower section 61 to a largest diameter at a top opening 64.

The top 64 of tubing 16' terminates at a point spaced downwardly by an interval in the axial direction, below the top of the upper flange portion 38' of the shroud double seal assembly 37'. A self-closing valve member 66 is secured in the interval, with its bottom contacting the top of tubing 16' and its top aligned with the top of portion 38'. Valve 66 may take the form of a disc-shaped diaphragm of elastomeric material secured to tubing 16' and shroud 17'. The diaphragm has a series of radially extending slits 67 which define a normally closed iris opening 68 having a plurality of contacting flaps 69 which yield downwardly to open valve 88 when tools are inserted into channel 15', but which rebound elastically when the same tools are removed, to return valve 66 to its closed valve position.

Valve 66 serves to prevent escape of fluid from the fundus when channel 15' is unoccupied. Tapered enlargement 62 provides room to accommodate flap deflections and acts as a guide to direct the leading ends of inserted tools downwardly toward the tubing lower end 61. If desired, the portion of shroud 17' surrounding the tapered section 62 of tubing 16' can be given a corresponding tapered enlargement or be uniformly expanded to accommodate the added dimensioning at the top to more fully support the expanded tubing 16' and the addition of valve 66.

Those skilled in the art to which the invention relates will appreciate that other substitutions and modifications can be made to the described embodiments, without departing from the spirit and scope of the invention as described by the claims below.

What is claimed is:

1. A cannula system for use in pars plana vitrectomy, said system including a cannula which can be anchored in the pars plana of an eyeball and which includes a working channel suitable for passing active surgical instruments into a vitreous cavity of the eyeball, and an adapter suitable for selectively alternatively utilizing said channel for communicating fluid from an infusion line into said vitreous cavity said cannula comprising:

a length of tubing having an open upper end, an open lower end, an outside diameter and a hollow interior defining said channel;

a shroud encasing said tubing, said shroud including means by which said cannula can be attached at a sclerotomy to a wall of an eyeball, with said lower end of said tubing inserted into a vitreous cavity of said eyeball; and a plurality of optical fibers having proximal and distal ends; said fibers running outside said tubing externally of said working channel and terminating within said shroud, with said proximal ends annularly, angularly spaced about said outside diameter at said lower end of said tubing;

and said adapter comprising:

a length of tubing having an open upper end for communication with an infusion line, an open lower end dimensioned and configured for insertion through said channel of said cannula tubing, and a hollow interior for delivery of infusion fluid from the infusion line into the vitreous cavity; and mating means for mating said adapter in sealing engagement with said cannula, when said adapter tubing is inserted through said cannula tubing channel, so that said lower end of said adapter tubing protrudes a distance beyond said lower end of said cannula tubing, for delivery of infusion fluid into the vitreous cavity at a discharge point located below said proximal ends of said fibers.

2. The system of claim 1, further including a plug suitable for selectively sealing said channel when said channel is not used for passing active surgical instruments or for communicating fluid by means of said adapter; said plug comprising:

a length of tubing having a closed upper end, an open lower end dimensioned and configured for insertion through said channel of said cannula tubing; and mating means for mating said plug in sealing engagement with said cannula, when said adapter tubing is inserted through said cannula tubing channel, so that said cannula tubing upper end is sealed by said plug.

3. The system of claim 1, wherein said cannula further comprises a seal assembly annularly disposed about said upper end of said cannula tubing; and wherein said mating means comprises a boot surrounding said adapter tubing and dimensioned, configured and adapted to snap over said seal assembly for sealing said cannula tubing upper end about said adapter tubing.

4. The system of claim 3, further including a plug suitable for selectively sealing said channel when said channel is not used for passing active surgical instruments or for communicating fluid by means of said adapter; said plug comprising:

a length of tubing having a closed upper end, an open lower end dimensioned and configured for insertion through said channel of said cannula tubing; and a boot surrounding said plug tubing and dimensioned, configured and adapted to snap over said double-seal assembly for sealing said cannula tubing upper end about said plug tubing.

5. The system of claim 1 including a plurality of cannulas, each having a length of tubing and a shroud as defined in claim 2, and a different plurality of optical fibers as defined in claim 2 respectively associated with each cannula; and said system further including a connector joining said distal ends of said respective pluralities of optical fibers of all of said cannulas to receive illumination from a common light source.

6. The system of claim 1, wherein said means by which said cannula can be attached at a sclerotomy comprises a suture pad having opposite laterally extending wings by which said cannula can be attached to an eyeball wall using a suture, and said shroud further includes an upwardly and outwardly angled sleeve portion above one of said wings; said optical fibers entering said shroud at said sleeve portion.

7. The system of claim 1, wherein said cannula length of tubing is a length of rigid plastic tubing; said shroud is a flexible plastic shroud; and said fibers are lightweight plastic fibers of numeric aperture greater than 0.6.

8. A cannula system for use in pars plana vitrectomy, said system including a cannula which can be anchored in the pars plana of an eyeball and which includes a working channel suitable for passing active surgical instruments into a vitreous cavity of the eyeball, and an adapter suitable for selectively alternatively utilizing said channel for communicating fluid from an infusion line into said vitreous cavity; said cannula comprising:
- a length of tubing having an open upper end, an open lower end, an outside diameter and a hollow interior defining said channel;
- a shroud encasing said tubing, said shroud including means by which said cannula can be attached at a sclerotomy to a wall of an eyeball, with said lower end of said tubing inserted into a vitreous cavity of said eyeball;
- a plurality of optical fibers having proximal and distal ends; said fibers running outside said tubing externally of said working channel and terminating within said shroud, with said proximal ends annularly, angularly spaced about said outside diameter at said lower end of said tubing; and
- a double-seal assembly annularly disposed about said upper end of said tubing;

and said adapter comprising:
- a length of tubing having an open upper end for communication with an infusion line, an open lower end dimensioned and configured for insertion through said channel of said cannula tubing, and a hollow interior for delivery of infusion fluid from the infusion line into the vitreous cavity; and
- a boot surrounding said adapter tubing and dimensioned, configured and adapted to snap over said double-seal assembly for sealing said cannula tubing upper end about said adapter tubing.

9. The system of claim 8, wherein said adapter tubing is dimensioned and configured relative to said cannula tubing so that, when said adapter tubing is inserted through said cannula tubing channel with said boot snapped over said double-seal assembly, said lower end of said adapter tubing protrudes a distance beyond said lower end of said cannula tubing, for delivery of infusion fluid into the vitreous cavity at a discharge point located below said proximal ends of said fiber.

10. The system of claim 8, including a plurality of cannulas, each having a length of tubing and a shroud as defined in claim 2, and a different plurality of optical fibers as defined in claim 2 respectively associated with each cannula; and said system further including a connector joining said distal ends of said respective pluralities of optical fibers of all of said cannulas to receive illumination from a common light source.

11. The system of claim 8, wherein said means by which said cannula can be attached at a sclerotomy comprises a suture pad having opposite laterally extending wings by which said cannula can be attached to an eyeball wall using a suture, and said shroud further includes an upwardly and outwardly angled sleeve portion above one of said wings; said optical fibers entering said shroud at said sleeve portion.

12. The system of claim 8, wherein said assembly is stepped in an axial direction and includes a circular ring-shaped flange upper portion of given outside diameter, a lesser outside diameter cylindrical intermediate portion, and a cylindrical lower portion of the same outside diameter as said upper portion.

13. The system of claim 12, wherein said lower portion includes a base; said assembly further comprises a circular ring-shaped shoulder surrounding said base; said boot comprises a slug enveloped by a downwardly opening cylindrical shell; said shell extending below said slug to present a downwardly opening cylindrical hollow of inside diameter slightly less than the outside diameter of said flange upper portion and lower portion of said assembly; said hollow being dimensioned in an axial direction to be the same as a corresponding axial extent of said assembly from said shoulder to a top of said flange upper portion; and said boot being dimensioned, configured and adapted to snap over said double-seal assembly with said slug brought adjacent to said top of said flange upper portion.

14. A cannula system for use in pars plana vitrectomy, said system including a cannula which can be anchored in the pars plana of an eyeball and which includes a working channel suitable for passing active surgical instruments into a vitreous cavity of the eyeball, and an adapter suitable for selectively alternatively utilizing said channel for communicating fluid from an infusion line into said vitreous cavity; said cannula comprising:
- a length of tubing having an open upper end, an open lower end, an outside diameter and a hollow interior defining said channel;
- a shroud encasing said tubing, said shroud including means by which said cannula can be attached at a sclerotomy to a wall of an eyeball, with said lower probe end of said tubing inserted into a vitreous cavity of said eyeball;
- a plurality of optical fibers having proximal and distal ends; said fibers running outside said tubing externally of said working channel and terminating within said shroud, with said proximal ends annularly, angularly spaced about said outside diameter at said lower end of said tubing; and
- self-closing valve means located within said channel for preventing escape of fluid from the vitreous cavity when said channel is unoccupied.

15. The system of claim 14, wherein said self-closing valve means comprises a diaphragm having a plurality of flaps defining a normally closed iris opening; said flaps yielding downwardly to open said iris opening when said instruments are passed through said channel, and rebounding elastically when the instruments are removed to return said iris to its closed position.

16. The system of claim 15, wherein said cannula tubing has an upper part including an enlarged channel portion having an upwardly and outwardly tapered inside diameter section, and wherein said diaphragm is positioned relative to said enlarged channel portion, so that said flaps yield downwardly into said tapered inside diameter section.

17. The system of claim 16, wherein said shroud includes an upper flange portion having a top; said upper end of said cannula tubing terminates at a point spaced downwardly by an interval in an axial direction, below said flange portion top; and said diaphragm is a disc-shaped diaphragm secured in said interval.

18. The system of claim 17, further comprising an adapter suitable for selectively utilizing said channel for communicating fluid from an infusion line into said vitreous cavity; said adapter comprising:
- a length of tubing having an open upper end for communication with an infusion line, an open lower end dimensioned and configured for insertion through said channel of said cannula tubing and through said iris opening, and a hollow interior for delivery of infusion fluid from the infusion line into the vitreous cavity; and
- mating means for mating said adapter in sealing engagement with said cannula, when said adapter tubing is inserted through said cannula tubing channel, so that said lower end of said adapter tubing protrudes a distance beyond said lower end of said cannula tubing, for delivery of infusion fluid into the vitreous cavity at a discharge point located below said proximal ends of said fibers.

19. The system of claim 18, wherein said cannula further comprises a seal assembly annularly disposed on said shroud about said upper end of said cannula tubing; and wherein said mating means comprises a boot surrounding said adapter tubing and dimensioned, configured and adapted to snap over said seal assembly for sealing said cannula tubing upper end about said adapter tubing, with said adapter tubing inserted through said iris opening.

20. The system of claim 19, wherein said cannula further comprises a seal assembly annularly disposed on said shroud about said upper end of said cannula tubing; and wherein said mating means comprises a boot surrounding said adapter tubing and dimensioned, configured and adapted to snap over said seal assembly for sealing said cannula tubing upper end about said adapter tubing, with said adapter tubing inserted through said iris opening.

* * * * *